US012606578B2

(12) United States Patent
Ding et al.

(10) Patent No.: US 12,606,578 B2
(45) Date of Patent: Apr. 21, 2026

(54) CRYSTAL FORM OF SPIROCYCLIC AMINE ARYL PHOSPHORUS OXIDE COMPOUND AND PREPARATION METHOD THEREFOR

(71) Applicant: Qilu Pharmaceutical Co., LTD., Jinan (CN)

(72) Inventors: Zhaofeng Ding, Jinan (CN); Qiang Fu, Jinan (CN)

(73) Assignee: QILU PHARMACEUTICAL CO., LTD., Jinan (CN)

( * ) Notice: Subject to any disclaimer, the term of this patent is extended or adjusted under 35 U.S.C. 154(b) by 0 days.

(21) Appl. No.: 19/100,372

(22) PCT Filed: Jul. 28, 2023

(86) PCT No.: PCT/CN2023/109709
§ 371 (c)(1),
(2) Date: Jun. 2, 2025

(87) PCT Pub. No.: WO2024/027565
PCT Pub. Date: Feb. 8, 2024

(65) Prior Publication Data

US 2025/0282804 A1 Sep. 11, 2025

(30) Foreign Application Priority Data

Aug. 1, 2022 (CN) ......................... 202210915901.8

(51) Int. Cl.
*C07F 9/6561* (2006.01)
*A61K 31/675* (2006.01)

(52) U.S. Cl.
CPC .......... *C07F 9/6561* (2013.01); *A61K 31/675* (2013.01); *C07B 2200/13* (2013.01)

(58) Field of Classification Search
CPC .................................................. C07B 2200/13
See application file for complete search history.

(56) References Cited

FOREIGN PATENT DOCUMENTS

| | | | | | |
|---|---|---|---|---|---|
| CN | 106928275 A | * | 7/2017 | .......... C07F 9/65615 |
| CN | 110407877 A | * | 11/2019 | .............. A61P 35/00 |
| WO | 2012139499 A1 | | 10/2012 | |
| WO | 2012140114 A1 | | 10/2012 | |
| WO | 2013138210 A1 | | 9/2013 | |
| WO | 2013148857 A1 | | 10/2013 | |
| WO | 2013177092 A1 | | 11/2013 | |
| WO | 2013192512 A1 | | 12/2013 | |
| WO | 2014002922 A1 | | 1/2014 | |
| WO | 2014006554 A1 | | 1/2014 | |
| WO | 2014025128 A1 | | 2/2014 | |
| WO | 201403316 A1 | | 3/2014 | |
| WO | 2016000581 A1 | | 1/2016 | |

OTHER PUBLICATIONS

International Search Report (ISR) for PCT/CN2023/109709 mailed Oct. 26, 2023 (5 pages).
Written Opinion (WO) for PCT/CN2023/109709 mailed Oct. 26, 2023 (6 pages).
X. Liu et al. "Discovery and preclinical evaluations of WX-0593, a novel ALK inhibitor targeting crizotinib-resistant mutations" Bioorganic & Medicinal Chemistry Letters, vol. 66, Apr. 11, 2022, p. 128730/1-128730/6.

* cited by examiner

*Primary Examiner* — Jeffrey S Lundgren
*Assistant Examiner* — Eric Tran
(74) *Attorney, Agent, or Firm* — Shumaker, Loop & Kendrick, LLP

(57) ABSTRACT

The present invention relates to a crystal form of a compound of Formula (I), i.e. (2-((5-chloro-2-((2-methoxy-4-(9-methyl-3,9-diaza-spiro[5.5]undecan-3-yl)phenyl)amino)pyrimidin-4-yl)amino)phenyl)dimethylphosphine oxide. The present invention further relates to a pharmaceutical composition of the crystal form, and the pharmaceutical use thereof and a preparation method therefor.

(I)

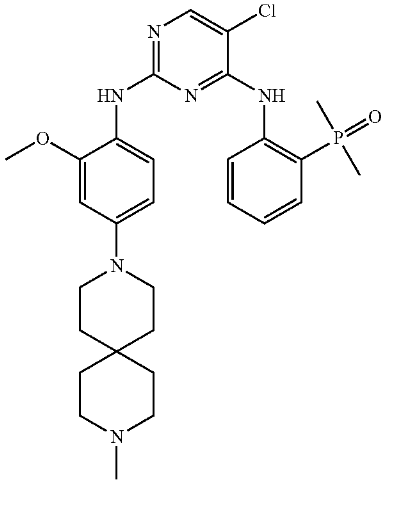

10 Claims, 4 Drawing Sheets

CRYSTAL FORM OF SPIROCYCLIC AMINE ARYL PHOSPHORUS OXIDE COMPOUND AND PREPARATION METHOD THEREFOR

The present application claims the priority of the Chinese Patent Application No. 202210915901.8, titled "CRYSTAL FORM OF SPIROCYCLIC AMINE ARYL PHOSPHORUS OXIDE COMPOUND AND PREPARATION METHOD THEREFOR", filed before the China National Intellectual Property Administration on Aug. 1, 2022, which is incorporated herein by reference in its entirety.

FIELD OF THE INVENTION

The present invention belongs to the field of pharmaceutical chemistry, and relates to a crystal form of spirocyclic amine aryl phosphorus oxide and preparation method therefor.

BACKGROUND OF THE INVENTION

Protein kinases play a dominant regulatory role in almost all types of cellular biological activity. These include proliferation, apoptosis, cytoskeletal rearrangement, differentiation, development, immune response, nervous system function and conduction. Moreover, many diseases and/or functional disorders are associated with the abnormal, aberrant or dysregulated activity of one or more protein kinases.

Anaplastic lymphoma kinase (ALK) is a part of the receptor tyrosine kinases (RTKs) protein family. The ALK gene provides an instruction for the protein of receptor tyrosine kinase to transmit signals from the cell surface into the cell through a signal transduction process. This process begins when the cell surface kinase is stimulated, and then the kinase dimerizes. After dimerization, the kinase is labeled with phosphate groups in a process called phosphorylation, which activates the kinase. The activated kinase can transfer phosphate groups to another protein in the cell and continue to transfer phosphorylation to a series of proteins downstream. This signaling pathway is important for many cellular processes, such as cell growth and division (proliferation) or maturation (differentiation).

Although the specific function of anaplastic lymphoma kinase is still unclear, it is generally believed that it can help regulate the proliferation of nerve cells during early development of nerve cells.

Mutations of the anaplastic lymphoma kinase ALK gene are changes of amino acids, the basic units of the protein. At least 16 mutations of the ALK gene have been identified in some patients with neuroblastoma and a tumor consists of immature nerve cells (neuroblasts). Neuroblastoma and other cancers are caused by gene mutation of some key genes (these key genes control the proliferation and differentiation of cells), which makes the growth and division of cells uncontrollable and therefore forms tumors.

The most common mutation in neuroblastoma is the substitution of arginine with glutamate at position 1275 (written as Arg1275Gln or R1275Q). The Arg1275Gln mutation is found in both hereditary and sporadic neuroblastomas and it is the only ALK gene mutation in common between hereditary and sporadic neuroblastomas.

Mutated or overexpressed anaplastic lymphoma kinases no longer require extracellular stimulation to phosphorylate. Therefore, kinases and downstream signaling pathways are continuously switched on (constitutive activation). Constitutive activation of anaplastic lymphoma kinases can increase the proliferation of immature nerve cells, and eventually lead to neuroblastoma. Rearrangements of the ALK gene on chromosome 2 increase the risk of developing other cancers. These rearrangements are somatic mutations, that is, somatic mutations exist throughout human life and only appear when cells become cancerous.

One type of rearrangement, called a translocation, is an exchange of genetic material between chromosome 2 and other chromosomes. At least 15 translocations involving the ALK gene have been identified in people with anaplastic large cell lymphoma (ALCL). Anaplastic large cell lymphoma is a rare form of cancer that occurs in immune cells called T cells. The most common translocation in ALCL occurs between chromosomes 2 and 5, called t (2,5). This translocation fuses the ALK gene with the NPM gene and forms an NPM-ALK fusion protein. In addition, at least seven ALK gene translocations have been identified in inflammatory myofibroblastoma (IMT). IMT is a rare cancer characterized by solid tumors composed of inflammatory cells and myofibroblasts, a type of cell that is important for wound healing. About half of people with IMT are involved in ALK gene translocations.

Another type of rearrangement, called inversion, occurs when chromosome 2 breaks into two parts, and the DNA of the resulting fragment is inverted and reinserted into the chromosome. Non-small cell lung cancer is the most common type of lung cancer, and in a small percentage of patients, chromosome 2 is inverted. This inversion fuses the ALK gene with another gene called EML4 to form an EML4-ALK fusion protein. The fusion protein generated by these rearranged genes has dual functions of anaplastic lymphoma kinase and chaperone protein.

ALK has always been a hot target for anti-tumor research and development, and Mesatros summarized progress in this area (Expert Opin. Ther Patents 2014, 24(4), 1). Crizotinib is the first ALK inhibitor approved by the FDA for the treatment of ALK-positive lung cancer. Although the initial response by Crizotinib was very effective, most patients relapsed in the first year of treatment due to drug resistance. On Apr. 29, 2014, FDA approved Ceritinib for the treatment of anaplastic lymphoma kinase (ALK)-positive metastatic non-small cell lung cancer (NSCLC), including patients who are responsive and resistant to Crizotinib. There are also some compounds that are being used in clinical research to treat cancer, such as Alectinib, AP-26113 and so on. Some heterocyclic compounds have also been disclosed for the treatment of various cancers. Patents include WO2014033136, WO2014025128, WO2014006554, WO2014002922, WO2013192512, WO2013177092, WO2013148857, WO2013138210, WO2012139499, WO2012140114.

However, although more than half of NSCLC patients have a good efficacy with Crizotinib, drug resistance will always occur over the time of medication, thus the drug loses its efficacy. Although ALK inhibitors have been vigorously developed for the treatment of non-small cell lung cancer in recent years, their efficacy is not satisfactory. Therefore, it is urgent to develop new, more effective and safe ALK inhibitors.

Spirocyclic amine aryl phosphorus oxides have been found to exhibit superior inhibitory activity against ALK, ALK mutants, and EGFR mutant enzymes than AP26113; and they also exhibit superior in vivo efficacy than the reference compound AzZP26113 in PDX models of NSCLC cell lines and Crizotinib drug-resistant PDX models obtained from ALK-positive patients. Therefore, further research and development of crystalline forms and preparation methods of such compounds, as well as pharmaceutical compositions in crystalline forms, may provide more effective treatment for diseases caused by aberrant ALK enzyme.

SUMMARY OF THE INVENTION

The present invention provides a crystal form Q4 of a compound of Formula (I), an X-ray powder diffraction spectrum of the crystal form Q4 has a characteristic peak at 1, 2, 3, 4 or 5 positions with 2θ values of 10.19, 14.27, 14.79, 16.14, 19.45 and 27.32, using Cu-$K_\alpha$ radiation, and the 2θ error range is ±0.2°.

(I)

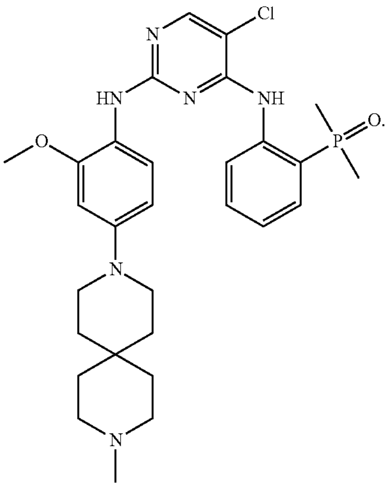

In some embodiments of the present invention, the X-ray powder diffraction spectrum of the crystal form Q4 of a compound of Formula (I) has a characteristic peak at 2θ values of 10.19, 14.27, 14.79, 16.14, 19.45 and 27.32, using Cu-$K_\alpha$ radiation, and the 2θ error range is ±0.2°.

In some embodiments of the present invention, the X-ray powder diffraction spectrum of the crystal form Q4 has a characteristic peak at 1, 2, 3, 4, 5, 6, 7, 8, 9, 10 or 11 positions with 2θ values of 10.19, 14.27, 14.79, 16.14, 17.99, 18.28, 19.45, 21.79, 22.12, 22.34, 24.40 and 27.32, using Cu-$K_\alpha$ radiation, and the 2θ error range is ±0.2°.

In some embodiments of the present invention, the X-ray powder diffraction spectrum of the crystal form Q4 has a characteristic peak at positions with 2θ values of 10.19, 14.27, 14.79, 16.14, 17.99, 18.28, 19.45, 21.79, 22.12, 22.34, 24.40 and 27.32, using Cu-$K_\alpha$ radiation, and the 2θ error range is ±0.2°.

In some embodiments of the present invention, the X-ray powder diffraction spectrum of the crystal form Q4 is substantially as shown in FIG. 1.

In some embodiments of the present invention, the analytical data of the X-ray powder diffraction peaks of the crystal form Q4 are shown in Table 1.

TABLE 1

Analytical data of the X-ray powder diffraction peaks of the crystal form Q4 of Formula (I)

| Number | 2θ angle [°] | Interplanar Spacing [Å] | Peak intensity [Counts] | Relative Peak Intensity [%] |
|---|---|---|---|---|
| 1. | 8.04 | 10.99 | 228.16 | 3.34 |
| 2. | 10.19 | 8.68 | 1553.70 | 22.76 |

TABLE 1-continued

Analytical data of the X-ray powder diffraction peaks of the crystal form Q4 of Formula (I)

| Number | 2θ angle [°] | Interplanar Spacing [Å] | Peak intensity [Counts] | Relative Peak Intensity [%] |
|---|---|---|---|---|
| 3. | 11.77 | 7.52 | 679.91 | 9.96 |
| 4. | 12.39 | 7.14 | 467.07 | 6.84 |
| 5. | 13.30 | 6.66 | 823.34 | 12.06 |
| 6. | 13.59 | 6.52 | 1152.35 | 16.88 |
| 7. | 14.27 | 6.21 | 6303.56 | 92.34 |
| 8. | 14.79 | 5.99 | 1601.49 | 23.46 |
| 9. | 15.58 | 5.69 | 727.06 | 10.65 |
| 10. | 16.14 | 5.49 | 2426.62 | 35.55 |
| 11. | 17.16 | 5.17 | 553.28 | 8.10 |
| 12. | 17.99 | 4.93 | 1784.96 | 26.15 |
| 13. | 18.28 | 4.85 | 1493.53 | 21.88 |
| 14. | 18.95 | 4.68 | 974.06 | 14.27 |
| 15. | 19.45 | 4.57 | 6826.73 | 100.00 |
| 16. | 20.01 | 4.44 | 805.70 | 11.80 |
| 17. | 20.43 | 4.35 | 192.63 | 2.82 |
| 18. | 21.24 | 4.18 | 747.69 | 10.95 |
| 19 | 21.62 | 4.11 | 1218.04 | 17.84 |
| 20. | 21.79 | 4.08 | 1526.50 | 22.36 |
| 21 | 22.12 | 4.02 | 2899.57 | 42.47 |
| 22 | 22.34 | 3.98 | 2325.67 | 34.07 |
| 23. | 23.55 | 3.78 | 295.89 | 4.33 |
| 24. | 24.05 | 3.70 | 328.64 | 4.81 |
| 25. | 24.40 | 3.65 | 1431.67 | 20.97 |
| 26. | 24.64 | 3.61 | 484.78 | 7.10 |
| 27. | 25.61 | 3.48 | 658.51 | 9.65 |
| 28. | 26.92 | 3.31 | 588.14 | 8.62 |
| 29. | 27.32 | 3.26 | 1994.06 | 29.21 |
| 30. | 28.14 | 3.17 | 292.71 | 4.29 |
| 31. | 28.76 | 3.10 | 598.23 | 8.76 |
| 32. | 29.81 | 3.00 | 634.85 | 9.30 |
| 33. | 30.77 | 2.91 | 446.89 | 6.55 |
| 34. | 31.37 | 2.85 | 162.52 | 2.38 |
| 35. | 31.85 | 2.81 | 241.42 | 3.54 |
| 36. | 32.68 | 2.74 | 382.27 | 5.60 |
| 37. | 33.13 | 2.70 | 436.61 | 6.40 |
| 38. | 33.95 | 2.64 | 275.47 | 4.04 |
| 39. | 34.53 | 2.60 | 92.78 | 1.36 |
| 40. | 35.13 | 2.55 | 215.97 | 3.16 |
| 41. | 35.96 | 2.50 | 174.16 | 2.55 |
| 42. | 37.65 | 2.39 | 211.57 | 3.10 |
| 43. | 38.19 | 2.36 | 119.31 | 1.75 |
| 44. | 39.45 | 2.28 | 284.94 | 4.17 |
| 45. | 41.40 | 2.18 | 124.72 | 1.83 |
| 46. | 41.94 | 2.15 | 224.16 | 3.28 |
| 47. | 43.88 | 2.06 | 122.03 | 1.79 |

In some embodiments of the present invention, a TGA-DSC spectrum of the crystal form Q4 has endothermic peaks at 208.5±2° C. and 224.5±2° C., and has an exothermic peak at 212.3±2° C.

In some embodiments of the present invention, the TGA-DSC spectrum of the crystal form Q4 is substantially as shown in FIG. 2.

In some embodiments of the present invention, a DVS spectrum of the crystal form Q4 is substantially as shown in FIG. 3.

The present invention further provides a method for preparing the crystal form Q4 of the compound of Formula (I), comprising: adding a crystal form A of the compound of Formula (I) to a solvent, stirring at room temperature, and filtering, the solvent is selected from the group consisting of water, an alcohols solvent, or a mixture thereof, preferably the solvent is methanol, water, or a mixed solvent thereof; wherein the mixed solvent of methanol and water is select from methanol/water (9:1 to 1:1, v/v), preferably methanol/water (4:1, v/v).

The present invention further provides another preparation method of the Q4 crystal form of the compound of Formula (I), comprising: adding the compound of Formula (I) to an alcohols solvent, heating and dissolving, filtering, and adding a Q4 crystal seed after cooling, then slowly cooling to −20° C. to −30° C., suction filtering and drying. The alcohols solvent is preferably methanol; and the slowly cooling temperature is preferably −10° C. to 10° C., more preferably −5° C.

The present invention further provides a pharmaceutical composition, comprising the crystal form Q4 of the compound of Formula (I) of any one of the above embodiments of the present invention, and optionally one or more pharmaceutically acceptable carriers.

The present invention further provides a use of the crystal form Q4 of the compound of Formula (I) of any one of the above embodiments in the manufacture of a medicament for treating and/or preventing a cancer related to ALK and/or EGFR and a mutation thereof, or a cancer to be treated by combining with inhibitors of ROS1, BRAF, c-MET, HER2, KRAS/MEK, PIK3CA, FDFR, DDR2 and/or VEGFR, or a cancer to be treated by combining with a cytotoxin.

The present invention further provides a use of the pharmaceutical composition in the manufacture of a medicament for treating and/or preventing a cancer related to ALK and/or EGFR and a mutation thereof, or a cancer to be treated by combining with inhibitors of ROS1, BRAF, c-MET, HER2, KRAS/MEK, PIK3CA, FDFR, DDR2 and/or VEGFR, or a cancer to be treated by combining with cytotoxins.

The present invention further provides a method for treating and/or preventing a cancer related to ALK and/or EGFR and a mutation thereof, or a cancer to be treated by combining with inhibitors of ROS1, BRAF, c-MET, HER2, KRAS/MEK, PIK3CA, FDFR, DDR2 and/or VEGFR, or a cancer to be treated by combining with a cytotoxin. The method comprises administering a therapeutically and/or preventively effective amount of the crystal form Q4 of the compound of Formula (I) to a patient.

In some embodiments of the present invention, the above cancer is non-small cell lung cancer.

DESCRIPTION AND DEFINITIONS

Unless otherwise stated, the terms and phrase used herein are intended to have the following meanings. A particular term or phrase without specifical definition should not be considered as indefinite or unclear, but should be understood according to its ordinary meaning.

The active compound represented by the crystal form Q4 of the compound of Formula (I) of the present invention may be used as the only anticancer agent or may be used in combination with one or more other antitumor agents. Combination therapy is achieved by administering the individual therapeutic components simultaneously, sequentially or separately.

The term "composition" refers to a product comprising ingredients in specified amounts, as well as a product resulting, directly or indirectly, from a combination of specified ingredients in specified amounts.

The crystal form of the compound of Formula (I) of the present invention can be prepared by those skilled in the art into a suitable pharmaceutical composition using known pharmaceutically acceptable carriers. The pharmaceutical composition can be formulated specifically for oral administration, parenteral injection or rectal administration in solid or liquid form.

The term "pharmaceutically acceptable carrier" refers to a medium generally acceptable in the art for the delivery of bioactive agents to animals, particularly mammals, according the administration and property of formulation, including, for example, adjuvants, excipients or vehicles, such as diluents, preservatives, fillers, flow modulators, disintegrants, wetting agents, emulsifiers, uspending agents, sweeteners, flavors, fragrances, antibacterial agents, antifungal agents, lubricants and dispersants. Pharmaceutically acceptable carriers are formulated according to a quantity of factors within the knowledge of those skilled in the art.

The pharmaceutical composition can be formulated into a number of dosage forms for ease of administration, for example, oral preparations (e.g., tablets, capsules, solutions, or suspensions); injectable preparations (e.g., injectable solutions or suspensions, or injectable dry powders ready for use after addition of a pharmaceutical vehicle prior to injection).

The term "therapeutically and/or preventively effective amount" refers to a sufficient amount of the compound or a pharmaceutically acceptable salt thereof of the present invention to treat a disorder in a reasonable effect/risk ratio suitable for any medical treatment and/or prevention. However, it should be recognized that the total daily dosage of the compound of Formula (I) or the pharmaceutically acceptable salt thereof of the composition of the present invention must be determined by the attending physician within the scope of reliable medical judgment For any specific patient, the specific therapeutically effective dose level shall depend on a variety of factors, including the disorder to be treated and the severity of the disorder; the activity of the specific compound used; the specific composition used; age, weight, general health condition, gender and diet of the patient; the administration time, route and excretion rate of the specific compound used; treatment duration; drugs used in combination with or simultaneously with the specific compounds used; and similar factors known in the medical field.

It is well known in the art that X-ray powder diffraction spectra have one or more measurement errors depending on minor variations in measurement conditions, and that the structures of crystallizations, crystals or crystal forms disclosed or claimed herein may exhibit similar, but not identical, analytical characteristics within reasonable error depending on test conditions, purity, equipments and other common variables known to those skilled in the art. For example, the diffraction angle (2θ) in powder X-ray powder diffraction generally produces an error within the range of ±0.20°. Therefore, the present invention includes not only crystallizations with completely identical diffraction angles in powder X-ray powder diffraction, but also crystallizations with identical diffraction angles within the error range of ±0.20°. The crystalline form of the compound of Formula (I) of the present invention is not limited to a crystal with an X-ray powder diffraction spectrum identical to the X-ray powder diffraction spectrum as shown in the drawings, and any crystal with an X-ray powder diffraction spectrum substantially identical to the X-ray powder diffraction spectrum as shown in the drawings belongs to the scope of the present invention.

In the present invention, examples of alcohols solvent or alcohol include but are not limited to methanol, ethanol, propanol, isopropanol and n-butanol.

In the present invention, the X-ray powder diffraction spectrum of the crystal form Q4 has a characteristic peak at 1, 2, 3, 4 or 5 positions with 2θ values of 10.19, 14.27, 14.79, 16.14, 19.45 and 27.32, and the 2θ error range is ±0.2°, wherein 1, 2, 3, 4 or 5 positions refer to that crystal forms with any of 1, 2, 3, 4 or 5 characteristic peaks identical to crystal form Q4, which are included in the scope of the present invention.

The "an X-ray powder diffraction spectrum substantially identical to the X-ray powder diffraction spectrum as shown in the drawings" appears herein. It should be understood that the term "substantially identical" as used herein is also intended to indicate that the 2θ angle values of the X-ray powder diffraction spectra may vary slightly due to the inherent experimental variations accompanying these measurements, both being of the same crystal form.

It should be understood that slightly different DSC spectrum and endothermic transition temperature readings may be given with different type of equipment or with different test conditions. DSC data can reflect the change in substance morphology, strong endothermic peaks can indicate that the substance has been dehydrated or desolvated, or has undergone crystal transformation or melting. When reflecting the molten state, the corresponding temperature is usually understood as the melting point of the substance. This value will be affected by the purity of the compound, the weight of the sample, the heating speed, the particle size and the calibration and maintenance of the test equipment. Those skilled in the art should understand that the temperature at which a substance changes from a solid state to a liquid state is usually a temperature range rather than a fixed point value. Therefore, the temperature corresponding to the endothermic peak or the melting point of the substance can be characterized by Onset value, Peak value or other reasonable values. The maximum endothermic transition temperature of the crystal form can be within the range of ±5.0° C. disclosed above, preferably within the range of ±2.0° C. of the specific values disclosed above.

The invention also analyzes the relationship between the degree of decomposition or sublimation and evaporation of crystal forms (weight loss) and temperature by using Thermogravimetry analysis (TGA). It should be understood that the same crystal form is affected by sample purity, particle size, different type of equipment, different test methods, etc., and there is a certain error in the obtained values. The temperature at which the crystal forms decompose, sublimate or evaporate may be within the range of ±3.0° C. of the specific values disclosed above, for example, within the range of ±2.0° C.

"Stability" of a crystal form includes "Chemical stability" and/or "Physical stability". "Chemical stability" refers to the degree of degradation reaction of the crystal form under certain temperature, humidity and light conditions. "Chemical stability" reflects the stability of the crystal form under storage conditions. "Physical stability" refers to the degree to which the crystal form is transformed into a solid form under certain conditions, such as high temperature, high humidity, grinding, tableting, desolvation, and solvent adsorption. Therefore, P stability" can reflect to a certain extent the degree to which the crystal form is stable during use of the preparation.

Description of hydroscopicity characteristics and definition of hygroscopic weight gain (Chinese Pharmacopoeia 2020 Edition, General Chapter 9103, Guidelines for Hydroscopicity Trials for Pharmaceuticals):

Deliquescence: absorb enough water to form liquid;

Extremely hygroscopic: the hygroscopic weight gain is not less than 15.0%;

Hygroscopic: hygroscopic weight gain is less than 15.0% but not less than 2.0%;

Mild hygroscopic: hygroscopic weight gain is less than 2.0% but not less than 0.2%;

Non-or almost non-hygroscopic: the hygroscopic weight gain is less than 0.2%.

Hydroscopicity directly affects the physicochemical stability of drugs. High hydroscopicity easily causes chemical degradation and crystal transformation. In addition, high hydroscopicity will reduce the fluidity of drugs, thus affecting the processing technology of drugs. Moreover, drugs with high hydroscopicity need to maintain low humidity in the process of production and storage, which puts forward higher requirements for production and requires high cost. More importantly, the high hydroscopicity is easy to cause changes in the content of active ingredients in drugs and affect the quality of drugs.

During storage, transportation and production, bulk drugs and preparations will encounter high temperature and humidity conditions caused by seasonal differences, climatic differences in different regions and weather factors. The crystal form with good stability is beneficial to avoid the influence of storage conditions on drug quality.

The transformation of crystal form will lead to changes in drug absorption, affect bioavailability, change in bioavailability, and even cause toxic and side effects of drugs. Good stability can ensure that basically no impurities are produced during storage of the drug, ensure that the quality of the bulk drug and the preparation is consistent and controllable, and minimize changes in drug quality caused by crystal form changes or impurities.

In the present invention, the "stirring" is accomplished by conventional methods in the art, such as magnetic stirring or mechanical stirring, and the stirring speed is 50 to 1800 rpm, wherein the magnetic stirring is preferably 300 to 900 rpm, and the mechanical stirring is preferably 100 to 300 rpm.

The "drying" may be carried out at room temperature or higher temperature. The drying temperature may range from room temperature to about 60° C., or to 50° C., or to 40° C. The drying time may range from 2 to 48 h, or overnight. Drying is carried out in a fume hood, blower oven or vacuum oven.

The crystalline structures of the present invention may be prepared by various methods comprising crystallization or recrystallization, sublimation from suitable solvents, growth from melts, transformation from one solid phase to another phase, crystallization from supercritical fluids and jet spraying, etc. The technology of crystallization or recrystallization of crystalline structure from solvent mixture comprises solvent evaporation, lowering the temperature of solvent mixture, seeding the supersaturated solvent mixture of the molecule and/or salt, freeze-drying the solvent mixture, adding anti-solvent to the solvent mixture, etc.

The unit of reaction temperature is in degrees Celsius or ° C. Unless otherwise specified, room temperature refers to 25±5° C.

Unless otherwise specified, Formula (I) or a compound of Formula (I) of the present invention refer to:

(I)

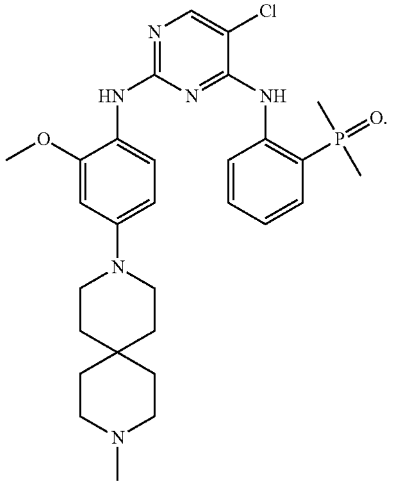

Instruments and Analysis Methods

1. X-Ray Powder Diffraction (XRPD)

Solid samples were analyzed by X-ray powder diffractometer (X' Pert PRO). An appropriate amount of test article fine powder was taken into the groove of specimen holder, and was pressed into flat and compact plane with a glass sheet. XRPD measurement parameters are shown in Table 2.

TABLE 2

| XRPD measurement parameters | |
|---|---|
| Instrument | PANalytical, X' Pert PRO type |
| Light source | Cu target |
| Scanning angle | 3 to 45° (2θ) |
| Scanning speed | 8°/min |
| Light tube voltage/current | 40 KV/40 mA |
| Divergence slit | 1/8° |

The solids were analyzed by Thermogravimetry and Differential Scanning Calorimetry using a Simultaneous Thermal Analyzer from METTLER TOLEDO. An appropriate amount of the test article was taken into a crucible with a small spoon, spread evenly, weighed, and heated according to the parameters listed in Table 3, and the data was analyzed by STARe.

TABLE 3

| Parameters of TGA-DSC | |
|---|---|
| Instrument | METTLER TOLEDO, TGA/DSC1 |
| Specimen plate | Platinum crucible |
| Temperature range | 25° C. to 400° C. |
| Heating rate | 10° C./min |
| Purging gas | Nitrogen |
| Flow rate | Balance chamber: 20 mL/min<br>Sample chamber: 50 mL/min |

2. Dynamic Vapor Sorption and Desorption Analysis (DVS)

The hydroscopicity of the samples was determined using a DVS Intrinsic dynamic vapor sorption analyzer. The samples were placed in a peeled sample basket, the instrument weighed automatically, and the samples were analyzed according to the parameters in Table 4.

TABLE 4

| Parameters of DVS | |
|---|---|
| Instrument | SMS, DVS Intrinsic |
| dm/dt | 0.002%/min |
| Sample weight | 10 to 30 mg |
| Drying/testing temperature | 40° C./25° C. |
| Cycle | Full cycle |
| Equilibrate time | 10 to 360 min |
| Data storage rate | 1 min |
| Gas and flow rate | $N_2$, 200 sccm |
| Post-running rate | 0 sccm |
| Step size | 10% RH |
| Method | Sorption: 0, 10, 20, 30, 40, 50, 60, 70, 80, 90<br>Desorption: 80, 70, 60, 50, 40, 30, 20, 10, 0 |

3. Nuclear Agnetic Resonance Spectrum ($^1$H-NMR)

Determination of $^1$H-NMR is performed by Bruker AVANCENEO 400 NMR instrument, and the solvent was deuterated dimethyl sulfoxide (DMSO-$d_6$).

4. High Performance Liquid Chromatography (HPLC)

Determination of HPLC is performed by Waters e2695 high performance liquid chromatograph to analyze the samples.

5. Particle Size Analysis (PSA)

Malvern's laser scattering particle size distribution analyzer was used to analyze the particle size of solid powder. An appropriate amount of solid powder was taken into a sampler, the samples were tested according to the parameters listed in Table 5, and the data was analyzed by Mastersizer-v3.60.

TABLE 5

| Parameters of PSA | | | | |
|---|---|---|---|---|
| Instrument | Model | Malvern Mastersizer 3000 | | |
| | Sampler name | AERO S | | |
| Detection condition | Particle type | Nonspherical | Analysis model | Universal (fine dry powder model) |
| | Particle refractive index | 1.520 | Particle absorption rate | 0.100 |
| | Background measurement time | 10 seconds | Sample measurement time | 10 seconds |
| | Dispersed air pressure | 1.2 Bar | Sampling rate | 50% |
| | Venturi tube type | High-energy Venturi tube | Shading range | 0.5% to 6% (shading filtering enabled) |

6. Scanning Electron Microscope

Instrument model: ZEISS Sigma 300 Scanning electron microscope.

Test method: An appropriate amount of the test article was taken, spread evenly on the conductive tape, sprayed gold, and observed under the electron microscope.

7. Tap Density

The tap density was measured by SVM203 Tapped Density Meter.

DETAILED DESCRIPTION

The present invention will be described in detail by the following embodiments, but this does not mean any adverse limitation the present invention. The compound of the present invention can be prepared by a variety of synthetic methods known to those skilled in the art, including the specific embodiments listed below, the embodiments formed by combining it with other chemical synthetic methods, and the equivalent alternatives known to those skilled in the art. The preferred embodiments include but are not limited to the examples of the present invention. It will be obvious to those skilled in the art that various changes and improvements can be made to specific embodiments of the present invention without departing from the spirit and scope of the present invention.

Unless otherwise specified, all the reactions in the present invention are carried out under continuous magnetic stirring in dry nitrogen or argon atmosphere, and the solvent is dry solvent, and the unit of the reaction temperature is degrees Celsius or ° C. Unless otherwise specified, room temperature refers to 25±5° C.

Reference Example 1: Preparation Method of a Crystal Form A of the Compound of Formula (I)

According to the method of Example 1 in reference CN110407877, 60.54 g of the compound of Formula (I), 218.0 g of absolute ethanol and 121.1 g of purified water were charged to a reaction kettle under the protection of nitrogen and stirring. The temperature was raised up to reflux, and the solution was stirred until dissolved while maintaining the temperature. The solution was thermally filtered, washed with a mixed solution of 9.7 g of absolute ethanol and 6.1 g of purified water, and the filtrate was transferred into a crystallization kettle. Under the protection of nitrogen, the solution was stirred at 80±5° C. for 25 min, cooled to 67.5±2.5° C. and then followed by an addition of crystal seeds. The mixture was cooled to 60±5° C. and stirred for 1 h, then cooled to 40±5° C. and stirred for 30 min while maintaining the temperature, and then cooled to 15±5° C. The system was kept at 15±5° C. for 35±5 min, then 302.7 g of purified water was added and stirred for 2.5 h while maintaining the temperature. The solution was filtered, the filter cake was washed with 120.1 g of purified water, and the resulted solid was dried in vacuum at 50 to 60° C. to obtain 55.59 g of solid, which was detected as the crystal form A by XRPD.

Example 1: Preparation Method of Crystal Form Q4 of the Compound of Formula (I)

Figure 1:
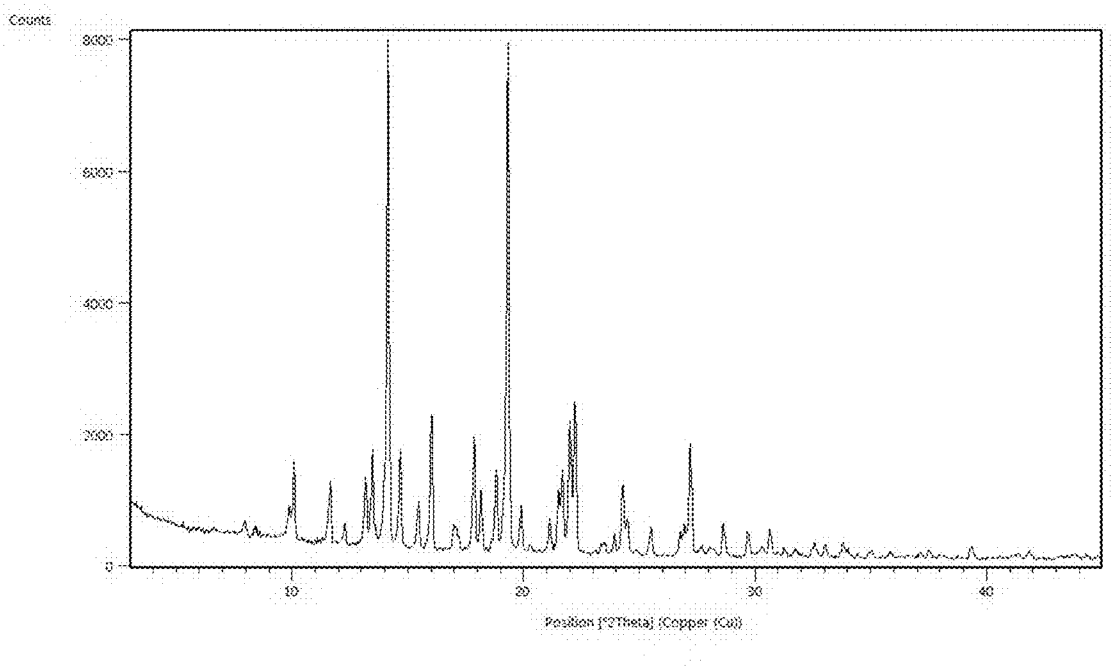
FIG. 1 shows an X-ray powder diffraction spectrum of a crystal form Q4 of the compound of Formula (I)

43.1 mg of the crystal form A of the compound of Formula (I) was added to 1 mL of methanol and stirred at room temperature for 23 h. The solution was filtered, and the resulted solid was characterized by XRPD, which was detected as the crystal form Q4 with an XRPD spectrum substantially as shown in FIG. 1.

Example 2: Preparation Method of the Crystal Form Q4 of the Compound of Formula (I)

2.72 g of the crystal form A of the compound of Formula (I) was added to 16 mL of methanol/water (4:1, v/v) and stirred at room temperature for 46 h. The solution was filtered, and dried in vacuum for 5 h. The resulted solid was characterized by XRPD and TGA/DSC, which was detected as the crystal form Q4 with an XRPD spectrum substantially as shown in FIG. 1.

Figure 2:
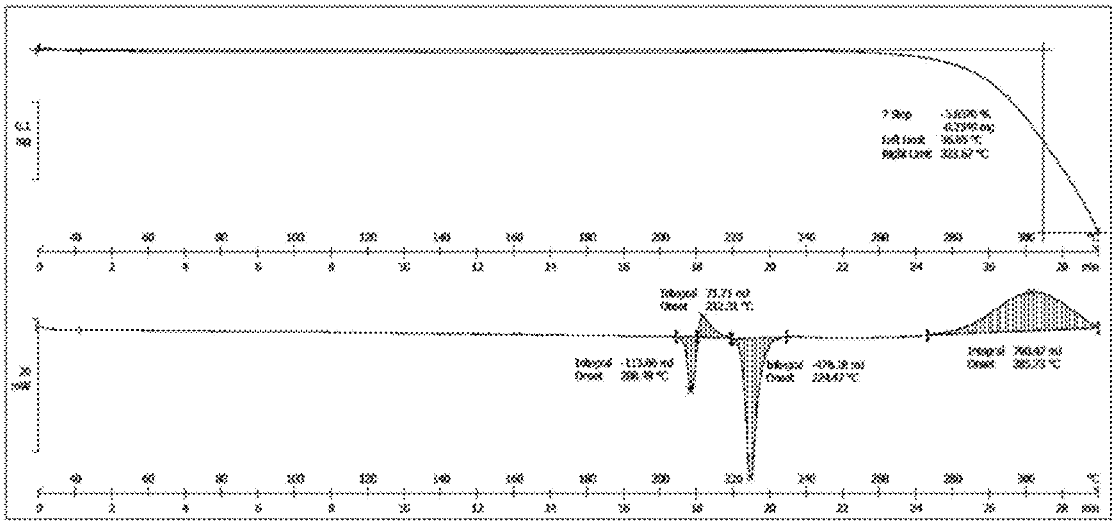
FIG. 2 shows a TGA-DSC spectrum of the crystal form Q4 of the compound of Formula (I)

The TGA-DSC spectrum is substantially as shown in FIG. 2, TGA shows no obvious weight loss before melting, indicating that the crystal form Q4 is anhydrous. There are endothermic peaks at 208.5° C., 224.5° C. and an exothermic peak at 212.3° C.

Example 3: Preparation Method of the Crystal form Q4 of the Compound of Formula (I)

0.12 g of the compound of Formula (I) was added into 360 mL of methanol, dissolved at 64° C. to get a clarified solution. The solution was thermally filtered. The mixture was cooled to 55° C., then 306.8 mg of Q4 crystal seed was added while maintaining the temperature for 0.5 h. The system was cooled slowly to −5° C. over 6 h, and kept at the temperature for 0.5 h. The mixture was suction filtered, and dried in vacuum at room temperature for 16 h. The resulted solid was characterized by XRPD, TGA-DSC, DVS, SEM and PSA, which was detected as the crystal form Q4 with an XRPD spectrum as shown in FIG. 1.

The TGA-DSC spectrum is shown in FIG. 2, TGA shows no obvious weight loss before melting, indicating that the crystal form Q4 is anhydrous. There are endothermic peaks at 208.5° C., 224.5° C. and an exothermic peak at 212.3° C.

Figure 3:
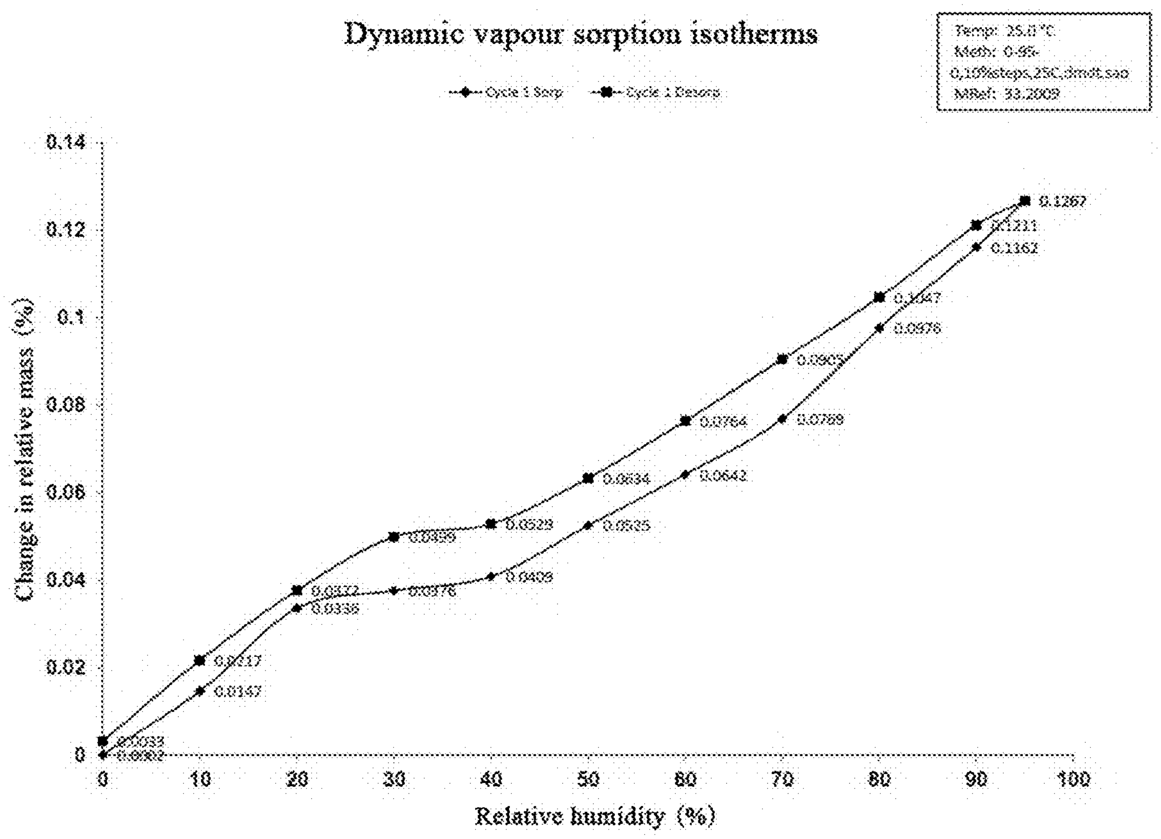
FIG. 3 shows a DVS spectrum of the crystal form Q4 of the compound of Formula (I)
Figure 4:
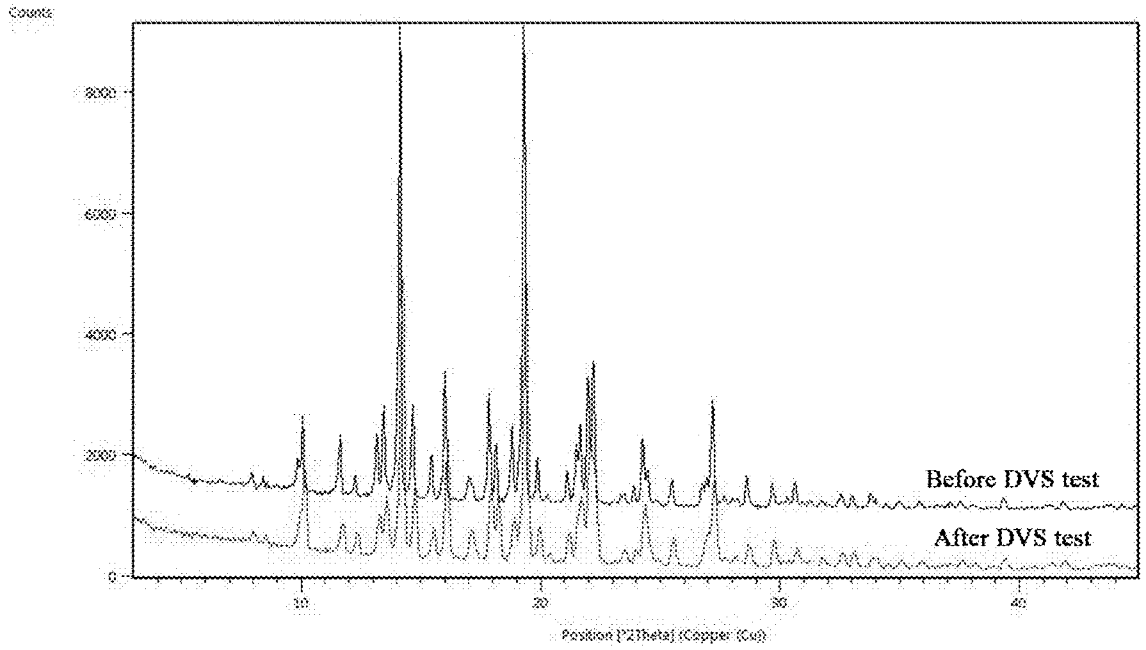
FIG. 4 shows the comparison of the XRPD spectrum of the crystal form Q4 of the compound of Formula (I) before and after DVS test.

The DVS spectrum is shown in FIG. 3. TGA shows the crystal form Q4 gaining 0.10% at 80% RH with non- or almost non-hygroscopic. The comparison of XRPD before and after DVS test is shown in FIG. 4, and there is no crystal transformation before and after the test.

Figure 5:
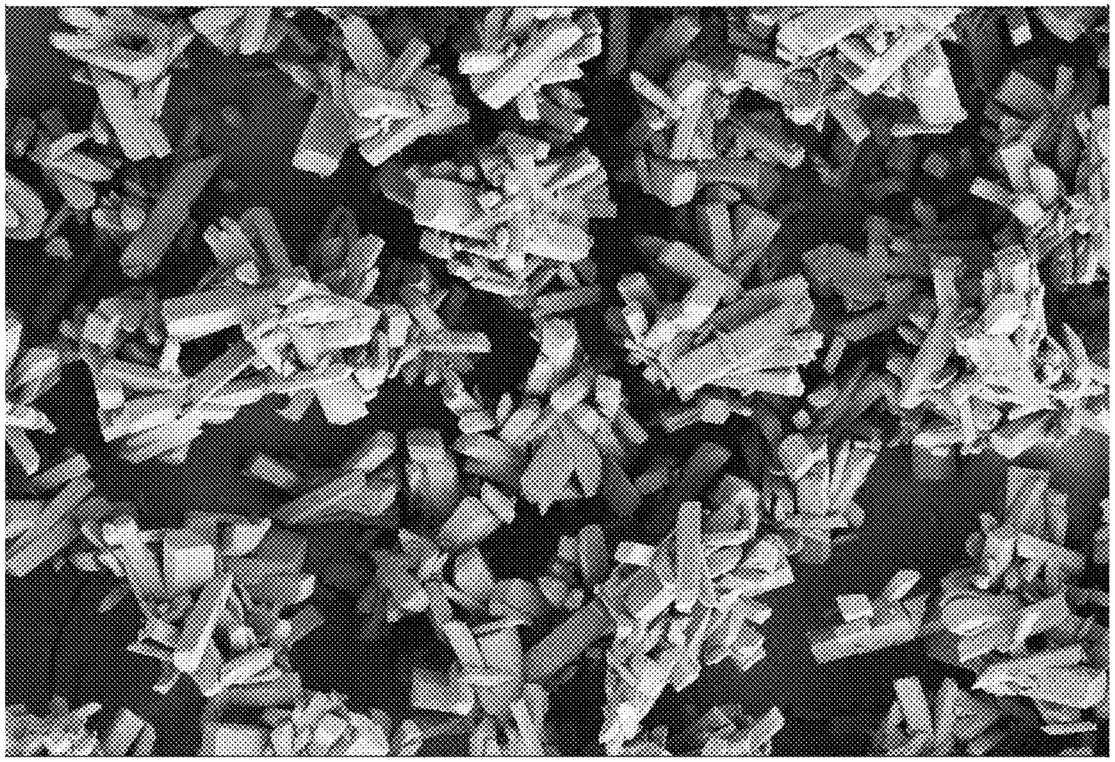
FIG. 5 shows a 500-fold enlarged SEM spectrum of the crystal form Q4 of the compound of Formula (I)

The SEM results are shown in FIG. 5, crystal Q4 is a rod-shaped crystal with uniform size distribution. In contrast, the SEM results of the crystal form A are shown in FIG. 6, and the crystal form A is a massive crystal with uneven size and serious agglomeration.

Figure 6:
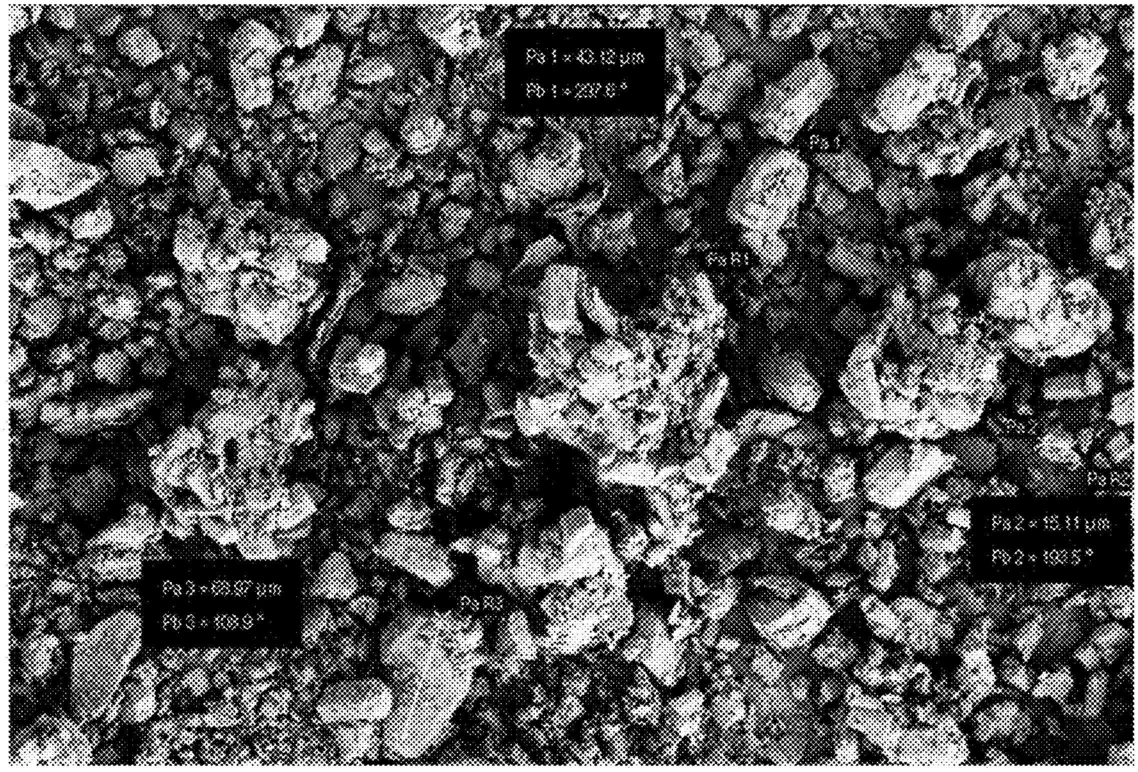
FIG. 6 shows a 500-fold enlarged SEM spectrum of a crystal form A of the compound of Formula (I)
Figure 7:
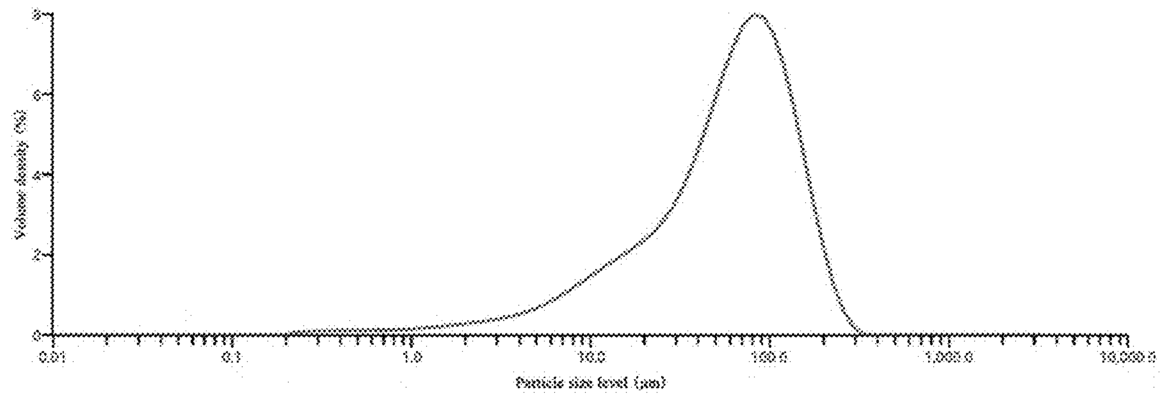
FIG. 7 shows a PSA spectrum of the crystal form Q4 of the compound of Formula (I).

The PSA results are shown in FIG. 6, and the D90 of the obtained crystal form Q4 is 145.2 μm, D50 is 62.6 μm, and D10 is 10.8 μm. The crystal form Q4 has a good single peak distribution.

Example 4: Flow Ability Test

Bulk density and tap density of bulk drugs with different crystal forms and particle sizes were tested, and Carr index was calculated. Specific results and flow ability evaluation are shown in Table 6.

TABLE 6

Comparison of flow ability between the crystal form Q4 and the crystal form A

| Crystal form | Crystal form Q4 | Crystal form Q4 | Crystal form A |
|---|---|---|---|
| Particle size of bulk D90 (μm) | 69.2 | 145.2 | 62 |

TABLE 6-continued

Comparison of flow ability between the crystal form Q4 and the crystal form A

| Crystal form | Crystal form Q4 | Crystal form Q4 | Crystal form A |
|---|---|---|---|
| Bulk density (g/ml) | 0.28 | 0.42 | 0.48 |
| Tap density (g/ml) | 0.37 | 0.51 | 0.70 |
| Carr index: (tap density-bulk density)/tap density (%) | 24.32 | 17.65 | 31.43 |
| Evaluation | fair flow ability | good or medium flow ability | poor flow ability |

The above results show that the crystal form Q4 of the present invention has a better flow ability compared with the crystal form A under the condition of substantially the same particle size, and the larger the particle size, the better the flow ability of the crystal form Q4. Therefore, compared with the crystal form A, the crystal form Q4 has obvious advantages in terms of powder mixing uniformity of bulk drugs and the preparation of solid preparations. The flow ability evaluation criteria are shown in Table 7 below.

TABLE 7

Flow ability evaluation criteria

| Carr index | Hausner ratio | Evaluation |
|---|---|---|
| ≤10% | 1.0 to 1.11 | very good |
| 11 to 15% | 1.12 to 1.18 | good |
| 16 to 20% | 1.19 to 1.25 | good or medium |
| 21 to 25% | 1.26 to 1.34 | fair |
| 26 to 31% | 1.35 to 1.45 | poor |
| 32 to 37% | 1.46 to 1.59 | very poor |
| >38% | >1.60 | very very poor |

Example 5: Stability Test

The stability of the crystal form Q4 of the compound of Formula (I) under high temperature, high humidity and light conditions was investigated. After placing for 5 days and 10 days under specific conditions, purity was tested by HPLC, and XRPD was performed. The experimental results are shown in Table 8.

TABLE 8

Stability test results of the crystal form Q4

| Placement conditions | Crystal form | Purity (%) | Related substances (%) Impurity LO RRT = 0.89 | Impurity QA RRT = 0.95 | Impurity LD RRT = 1.10 | Impurity LP RRT = 1.16 | Impurity LG RRT = 1.98 |
|---|---|---|---|---|---|---|---|
| Start | Crystal form Q4 | 99.90 | 0.01 | 0.01 | ND | 0.02 | 0.03 |
| 40° C.-5 D | Crystal form Q4 | 99.88 | 0.01 | 0.01 | ND | 0.02 | 0.04 |
| 40° C.-10 D | Crystal form Q4 | 99.87 | 0.01 | 0.01 | ND | 0.03 | 0.04 |
| 60° C.-5 D | Crystal form Q4 | 99.86 | 0.01 | 0.01 | ND | 0.02 | 0.04 |
| 60° C.-10 D | Crystal form Q4 | 99.88 | 0.01 | 0.01 | ND | 0.02 | 0.04 |
| 75RH-5 D | Crystal form Q4 | 99.88 | 0.01 | 0.01 | ND | 0.01 | 0.04 |
| 75RH-10 D | Crystal form Q4 | 99.88 | 0.01 | 0.01 | ND | 0.02 | 0.04 |

TABLE 8-continued

Stability test results of the crystal form Q4

| Placement conditions | Crystal form | Purity (%) | Related substances (%) Impurity LO RRT = 0.89 | Impurity QA RRT = 0.95 | Impurity LD RRT = 1.10 | Impurity LP RRT = 1.16 | Impurity LG RRT = 1.98 |
|---|---|---|---|---|---|---|---|
| 90RH-5 D | Crystal form Q4 | 99.87 | 0.02 | 0.01 | ND | 0.01 | 0.04 |
| 90RH-10 D | Crystal form Q4 | 99.83 | 0.01 | 0.01 | ND | 0.03 | 0.04 |
| Light-5 D | Crystal form Q4 | 99.82 | 0.03 | 0.01 | ND | 0.02 | 0.04 |
| Light-10 D | Crystal form Q4 | 99.86 | 0.03 | 0.01 | ND | 0.02 | 0.03 |

The crystal form Q4 has no obvious degradation under high temperature, high humidity and light conditions, and has a good stability.

Example 6: Hydroscopicity Experiment

According to "Guidelines for Hydroscopicity Trials for Pharmaceuticals" in Chinese Pharmacopoeia 2020 Edition, the data of water sorption/desorption of the crystal form Q4 of the compound of Formula (I) were tested. The DVS curve of the crystal form Q4 is shown in FIG. 3, and the hydroscopicity data is shown in Table 9.

TABLE 9

Hydroscopicity of the crystal form Q4

| Sample | 80% RH weight gain | 90% RH weight gain | Evaluation of hydroscopicity |
|---|---|---|---|
| Crystal form Q4 | 0.10% | 0.12% | Non- or almost non-hygroscopic |

From the hydroscopicity data, it can be seen that the crystal form Q4 has a weight gain of 0.10% at 80% RH humidity condition, which belongs to non- or almost non-hygroscopic. By comparison, it can be seen that the hygroscopic weight gain of crystal form Q4 is less than that of the crystal forms A, B and C disclosed in reference CN110407877 (0.17%, 0.70% and 0.62% of the weight gain under 90% RH humidity condition, respectively). It can be seen that the crystal form Q4 has less hydroscopicity than the crystal forms A, B and C, and does not have defects such as chemical degradation, crystal form transformation and poor flow ability caused by large hydroscopicity, thus it is more beneficial to the processing technology of drugs.

Example 7: Solubility Experiment

At 37° C., appropriate amounts of the crystal form Q4 and crystal form A of the compound of Formula (I) were taken and dispersed in water, artificial gastric fluid (SGF, Simulated Gastric Fluid), artificial intestinal fluid under fed state (FeSSIF, Fed State Simulated Intestinal Fluid) and artificial intestinal fluid under fasted state (FaSSIF, Fasted State Simulated Intestinal Fluid) respectively to prepare suspension, and after equilibration at 200 rpm for 24 h, the content (mg/mL) of the sample in the solution were tested by HPLC and the samples in the solution were tested by XRPD, respectively. The results are shown in Table 10.

TABLE 10

Equilibrium solubility and XRPD test results of the crystal form Q4 and the crystal form A in four media

| | Water | | SGF (pH 1.8) | | FeSSIF (pH 5.0) | | FaSSIF (pH 6.5) | |
|---|---|---|---|---|---|---|---|---|
| Sample | Solubility (mg/mL) | XRPD test results | Solubility (mg/mL) | XRPD test results | Solubility (mg/mL) | XRPD test results | Solubility (mg/mL) | XRPD test results |
| Crystal form A | 0.04 | A | 9.30 | A | 23.60 | A | 4.56 | A |
| Crystal form Q4 | 0.04 | Q4 | 9.28 | Q4 | 23.56 | Q4 | 5.75 | Q4 |

The solubility of the crystal form Q4 in water, SGF and FeSSIF is similar to that of the crystal form A. The solubility of the crystal form Q4 in FaSSIF is better than that of the crystal form A, indicating that the crystal form Q4 has better bioavailability under fasting state. The crystal form Q4 and the crystal form A do not transform before and after the test, and have a good stability.

What is claimed is:

1. A crystal form Q4 of a compound of Formula (I), (I)

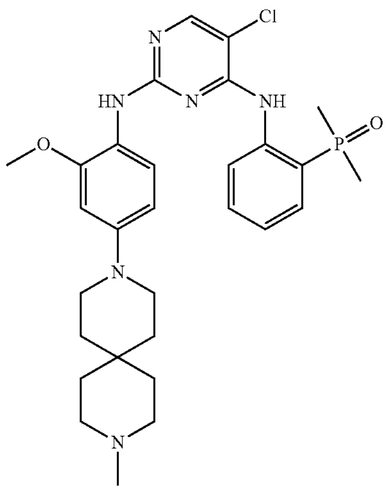

wherein an X-ray powder diffraction spectrum of the crystal form Q4 has a characteristic peak at 2θ values of 10.19, 14.27, 14.79, 16.14, 19.45 and 27.32, using Cu-$K_\alpha$ radiation, and the 2θ error range is ±0.2°.

2. The crystal form Q4 according to claim 1, wherein the X-ray powder diffraction spectrum of the crystal form Q4 has a characteristic peak at 2θ values of 10.19, 14.27, 14.79, 16.14, 17.99, 18.28, 19.45, 21.79, 22.12, 22.34, 24.40 and 27.32, using Cu-$K_\alpha$ radiation, and the 2θ error range is ±0.2°.

3. The crystal form Q4 according to claim 1, wherein a TGA-DSC spectrum of the crystal form Q4 has an endothermic peak at 208.5±2° C. and 224.5±2° C., and has an exothermic peak at 212.3±2° C.

4. A method for preparing the crystal form Q4 according to claim 1, comprising adding the crystal form A of the compound of Formula (I) to a solvent, stirring at room temperature, and filtering, wherein the solvent is selected from the group consisting of water, an alcohols solvent, or a mixture thereof; or the method comprises adding the compound of Formula (I) to an alcohols solvent, heating and dissolving, filtering, and adding a crystal seed of the crystal form Q4 after cooling, then slowly cooling to −20° C. to −30° C., suction filtering and drying.

5. A pharmaceutical composition, comprising the crystal form Q4 according to claim 1, and optionally one or more pharmaceutically acceptable carriers.

6. A method for treating a cancer related to ALK and/or EGFR and a mutation thereof, a cancer to be treated by combining with inhibitors of ROS1, BRAF, c-MET, HER2, KRAS/MEK, PIK3CA, FDFR, DDR2 and/or VEGFR, or a cancer to be treated by combining with a cytotoxin, comprising administering the crystal form Q4 according to claim 1 to a subject.

7. The method according to claim 6, wherein the cancer is non-small cell lung cancer.

8. The method according to claim 4, wherein the solvent is methanol or a mixed solvent of methanol and water.

9. The method according to claim 4, wherein the alcohols solvent is methanol.

10. The method according to claim 8, wherein the solvent is a mixed solvent of methanol and water in a volume ratio of 9:1 to 1:1.

* * * * *